United States Patent [19]

Copeland et al.

[11] Patent Number: 5,756,506
[45] Date of Patent: May 26, 1998

[54] SINGLE HIGH DOSE FLUOROQUINOLONE TREATMENT

[75] Inventors: Dennis D. Copeland, Spring Hill; Kathleen M. Ewert, McLouth; Terry S. Wollen, Lenexa, all of Kans.

[73] Assignee: Bayer Corporation, Pittsburgh, Pa.

[21] Appl. No.: 863,384

[22] Filed: May 27, 1997

Related U.S. Application Data

[63] Continuation of Ser. No. 496,117, Jun. 27, 1995, abandoned.

[51] Int. Cl.$^6$ .......................... A61K 31/495; A61K 31/50; A61K 31/535

[52] U.S. Cl. .......................... 514/254; 514/230.2

[58] Field of Search .......................... 514/254, 230.2

[56] References Cited

U.S. PATENT DOCUMENTS 4,659,603  4/1987  Grohe et al. .................. 424/88
4,670,444  6/1987  Grohe et al. .................. 514/300

OTHER PUBLICATIONS

Kofer et al. Medline Abstracts, abstract no. 93127161, Dec. 1992.
Antimicrobial Agents and Chemotherapy, Mar., 1993, pp. 483–490, Drusano et al.
J. vet., Narmacol. Therap. 18, 357–362, 1995, Kaartinen et al.
Am J Vet Res. vol. 56, No. 9, Sep., 1995, Meinen et al.
P. Richez et al. 6th EAVPT Congress, Aug. 1994, pp. 232–234.

*Primary Examiner*—William R. A. Jarvis
*Attorney, Agent, or Firm*—Joseph C. Gil; Godfried R. Akorli

[57] ABSTRACT

The present invention relates to treatment of bacterial infections in animals with fluoroquinolones. More specifically, the present invention relates to the use of fluoroqunolones in a single high dose to replace multiple lower doses.

7 Claims, No Drawings

SINGLE HIGH DOSE FLUOROQUINOLONE TREATMENT

This application is a continuation of application Ser. No. 08/496,117, filed Jun. 27, 1995 now abandoned.

BACKGROUND OF THE INVENTION

1. Field of the Invention

The present invention relates to treatment of animals with fluoro-quinolones. More specifically, the present invention relates to the use of fluoroquinolones in a single high dose to replace multiple lower doses.

2. Brief Description of the Prior Art

Generally, the art teaches the use of fluoroquinolones in treating diseases such as bovine respiratory disease in feed-lot cattle. Daily doses for three to five consecutive days have been used to treat bovine respiratory and other diseases. Heretofore, the art has not taught the use of a single elevated dose of a fluoroquinolone to treat the likes of bovine respiratory disease. Single treatment antimicrobials other than fluoroquinolones are effective based on specific formulations which prolong the release of active ingredient and extend the blood and tissue levels of animals treated therewith. Failure to use a single high dose might have been due to the perceived need for a special formulation to prolong the blood levels.

By the present invention, there is provided a single high dose treatment of fluoroquinolone to replace repeated treatments without the need for special prolonged release formulations.

DESCRIPTION OF THE INVENTION

In accordance with the foregoing, the present invention encompasses an: improved process for treating subject animals by administering thereto a pharmaceutically effective amount of a fluoroquinolone, the improvement comprising a high dose equivalent to the total dose normally administered daily for several days.

Non-limiting examples of fluoroquinolones can be selected from the group consisting of enrofloxacin, amifloxacin, benofloxacin, danofloxacin, difloxacin, fleroxacin, fleroxacin, lomefloxacin, marbofloxacin, norfloxacin, ofloxacin, perfloxacin, ruflocaxin, sarafloxacin and temafloxacin. The fluoroquinolone preferred herein is enrofloxacin.

Enrofloxacin is a fluoroquinolone carboxylic compound or a salt thereof. More specifically, enrofloxacin is 1-cyclopropyl-7-(4-ethyl-1-piperazinyl)-6-fluoro-1,4-dihydro-4-oxo-3-quinoline carboxylic acid. Suitable salts are those of inorganic or organic acids selected from the group consisting of hydrochloric acid, hydrobromic acid, hydroiodic acid, sulfuric acid, phosphoric acid, acetic acid, succinic acid, phosphonic acid, malic acid, sodium hydroxide, potassium hydroxide, aluminum hydroxide, piperidine, morpholine, ethylamine, and triethylamine. The enrofloxacin and a method of preparing the same is described in U.S. Pat. No. 4,670,444 which is incorporated herein by reference.

In accordance with the invention, the enrofloxacin can be formulated into a pharmaceutically effective composition that can be administered in a single high dose. The composition can be prepared by art-known techniques, for example, by mixing the active ingredient with a physiologically acceptable carrier. The carrier can be water and/or a member of the class selected from the group consisting of amino acids, metal hydroxides, alcohols, organic and inorganic acids and glycols. Specific examples thereof can be selected from the group consisting of arginine, potassium hydroxide, benzyl alcohol, citric acid, hydrochloric acid and propylene glycol. The resulting pharmaceutical composition is typically an injectable solution containing from 10 mg/mL to 350 mg/mL and preferably 20 mg/mL to 150 mg/mL and most preferably 100 mg/mL of the active ingredient comprising the enrofloxacin.

In treating animals in accordance with the invention, the pharmaceutical composition is administered to the subject animals in a high single dose of 5 mg/kg to 30 mg/kg and preferably 7.5 mg/kg to 12.5 mg/kg.

Surprisingly, it has been found that a single, high dose of fluoroquinolones can be administered to effectively treat disease such as bovine respiratory disease, e.g. *Pasteurella haemolytica* or *Pasteurella multocida* and swine pneumonia such as *Actinobacillius pleuropneumonia*.

The invention is further illustrated by the following non-limiting examples.

EXAMPLES

Example #1

In this example, a formulation of enrofloxacin was used to treat bovine respiratory disease. The formulation of enrofloxacin was administered to subject animals subcutaneously either as a repeated daily dose of 2.5 mg/kg or a single dose of 7.5 or 15.0 mg/kg. Response to treatment was determined by mortality (ability to prevent death), success (clinical cure), percent lung consolidation (percent of damaged lung remaining following treatment) and weight gain (healthy animals gain better than sick animals). The results are presented in the following table:

| Number Animals | Dose | Number Mortality | Number Success | % Lung Consolidation | Weight Gain (kg) |
|---|---|---|---|---|---|
| 12 | 0 | 4 | 0 | 37.9 | 2.3 |
| 12 | 2.5 × 3 days | 0 | 7 | 13.9 | 7.7 |
| 12 | 7.5 × 1 day | 0 | 7 | 15.9 | 6.7 |
| 12 | 15.0 × 1 day | 0 | 8 | 14.4 | 5.8 |

The three treatment groups were not significantly different from each other in any of the variables examined.

Example #2

In this example a formulation of enrofloxacin was used to treat bovine respiratory disease. The formulation of enrofloxacin was given to subject animals either as a repeated daily dose of 2.5 mg/kg per day or as a single dose of 5.0 mg/kg or 7.5 mg/kg. These treatment groups were compared to a negative control (no treatment) and an established prolonged action single injection of macrolide or tilmacosin. The results are presented in the following table:

| Number of Animals | Dose | Number Mortality | Number Success |
|---|---|---|---|
| 14 | 0 | 3 | 2 |
| 27 | 5.0 × 1 day | 0 | 8 |
| 28 | 7.5 × 1 day | 0 | 14 |

-continued

| Number of Animals | Dose | Number Mortality | Number Success |
|---|---|---|---|
| 28 | 2.5 × 3 days | 0 | 13 |
| 28 | Tilmicosin | 1 | 13 |

The results demonstrate 7.5 mg/kg of enrofloxacin given as a single injection is as effective as 3 daily injections of 2.5 mg/kg enrofloxacin. It is also as effective as a single injection of the long acting tilmicosin.

Example #3

In this example a formulation of enrofloxacin was used to treat pleuropneumonia in swine. The formulation of enrofloxacin was administered to the subject animals subcutaneously either as a repeated daily dose of 2.5 mg/kg or as a single dose of 2.5, 5.0, 7.5 or 10 mg/kg.

The results are presented in the following table:

| Number Animals | Dose | Number Mortality | Number Success | % Lung Consolidation | Weight Gain (lbs) |
|---|---|---|---|---|---|
| 12 | 0 | 2 | 1 | 22 | 5 |
| 12 | 2.5 × 1 day | 0 | 6 | 2 | 15 |
| 12 | 5.0 × 1 day | 0 | 9 | 12 | 19 |
| 12 | 7.5 × 1 day | 0 | 10 | 5 | 18 |
| 12 | 10.0 × 1 day | 0 | 9 | 7 | 20 |
| 12 | 2.5 × 3 days | 0 | 8 | 4 | 18 |

The results clearly demonstrate that 7.5 and 10 mg/kg given as a single injection are as effective as 3 daily injections of 2.5 mg/kg enrofloxacin.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for treating a bacterial infection in an animal in need thereof comprising administering to said animal a pharmaceutically effective composition comprising a fluoroquinolone, an ester, or a salt thereof in one high dose, single treatment.

2. A composition of claim 1 wherein the fluoroquinolone is selected from the group consisting of amifloxacin, benofloxacin, danofloxacin, difloxacin, enrofloxacin, flerofloxacin, fleroxacin, lomefloxacin, marbofloxacin, norfloxacin, ofloxacin, perfloxacin, rufloxacin, sarafloxacin, and temafloxacin.

3. The composition of claim 2 wherein the fluoroquinolone is enrofloxacin.

4. The process of claim 1, wherein the bacterial infection is bovine respiratory disease.

5. The process of claim 4 wherein the bovine respiratory disease is caused by Pasteurella, haemolytica or Pasteurella multocida.

6. The process of claim 1, wherein the bacterial infection is swine pneumonia.

7. The process of claim 6 wherein the swine pneumonia is caused by *Actinobacillius pleuropneumonia*.

* * * * *